US00PP27940P2

(12) United States Plant Patent
Jandrew

(10) Patent No.: US PP27,940 P2
(45) Date of Patent: Apr. 25, 2017

(54) ***IPOMOEA* PLANT NAMED 'KPOZ0001'**

(50) Latin Name: ***Ipomoea batatas* (L.) Lam**
Varietal Denomination: KPOZ0001

(71) Applicant: SYNGENTA PARTICIPATIONS AG, Basel (CH)

(72) Inventor: Jason Jandrew, Nipomo, CA (US)

(73) Assignee: Syngenta Participations AG, Basel (CH)

( * ) Notice: Subject to any disclaimer, the term of this patent is extended or adjusted under 35 U.S.C. 154(b) by 24 days.

(21) Appl. No.: 14/756,831

(22) Filed: Oct. 20, 2015

(51) Int. Cl.
*A01H 5/12* (2006.01)

(52) U.S. Cl.
USPC ..... Plt./263.1

(58) Field of Classification Search
USPC ..... Plt./258, 263.1, 373
See application file for complete search history.

*Primary Examiner* — Susan McCormick Ewoldt
(74) *Attorney, Agent, or Firm* — Dale Skalla

(57) ABSTRACT

A new *Ipomoea* plant named 'KPOZ0001', particularly distinguished by compact and mounding plant habit, then becomes more outwardly trailing with age, vigorous, freely branching with dense palmately shaped foliage. The large foliage displays shades of olive green, bronze and reddish purple. Flowers, when present, are medium sized pale lavender pink.

1 Drawing Sheet

Latin name of the genus and species of the plant claimed: *Ipomoea batatas* (L.) Lam.

Varietal denomination: 'KPOZ0001'.

BACKGROUND OF THE NEW PLANT

The present invention comprises a new *Ipomoea*, botanically known as *Ipomoea batatas* (L.) Lam and hereinafter referred to by the variety name 'KPOZ0001'.

'KPOZ0001' is a product of a planned breeding program for the development of Ornamental Sweet Potato cultivars. These plants are grown, not for their flowers, but for their foliage and plant habit characteristics. These plants flower very rarely and then only under strict short day lengths.

The new cultivar 'KPOZ0001' has compact and mounding plant habit, then becomes more outwardly trailing with age, vigorous, freely branching with dense palmately shaped foliage. The large foliage displays shades of olive green, bronze and reddish purple. Flowers, when present, are medium sized pale lavender pink.

'KPOZ0001' originates from an open pollination hybridization in a controlled breeding program in Gilroy, Calif., USA. The pollinations were made in the summer of 2008.

The female parent is the commercial variety 'Sweet Caroline Purple' (U.S. Plant Pat. No. 14,912). 'Sweet Caroline Purple' has a more broadly spreading plant habit, much deeper purple foliage color and produces flowers more readily than 'KPOZ0001'.

The male parent of 'KPOZ0001' is unknown.

The resulting seeds were sown in October 2008 and 'KPOZ0001' was selected as one flowering plant within the progeny of the stated cross in January 2009 in a greenhouse in Gilroy, Calif.

The first act of asexual reproduction of 'KPOZ0001' was accomplished when vegetative cuttings were propagated from the initial selection in March 2009 in a controlled environment in Gilroy, Calif.

BRIEF SUMMARY OF INVENTION

Horticultural examination of plants grown from cuttings of the plant initiated in May 2009 in Gilroy, Calif., and continuing thereafter, has demonstrated that the combination of characteristics as herein disclosed for 'KPOZ0001' are firmly fixed and are retained through successive generations of asexual reproduction.

'KPOZ0001' has not been observed under all possible environmental conditions. The phenotype may vary significantly with variations in environment such as temperature, light intensity, and day length.

Plant Breeder's Rights for this cultivar have not yet been applied for. 'KPOZ0001' has not been made publicly available more than one year prior to the filing of this application.

The following traits have been repeatedly observed and are determined to be basic characteristics of the new variety. The combination of these characteristics distinguishes this Ipomoea as a new and distinct variety.

BRIEF DESCRIPTION OF THE PHOTOGRAPHS

The accompanying photographic drawings show typical foliage characteristics of 'KPOZ0001' with colors being as true as possible with an illustration of this type.

Figure 1:
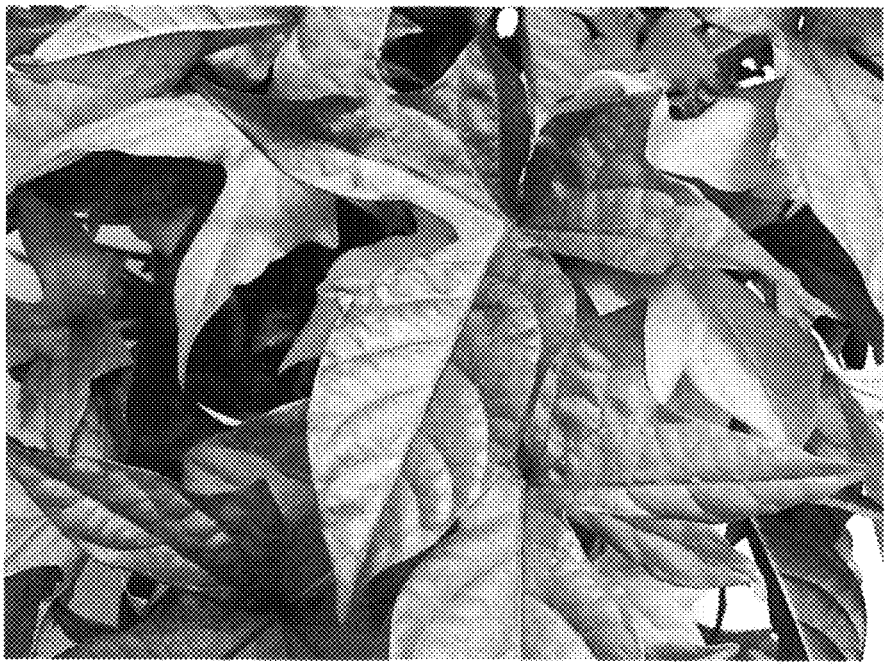
Figure 2:
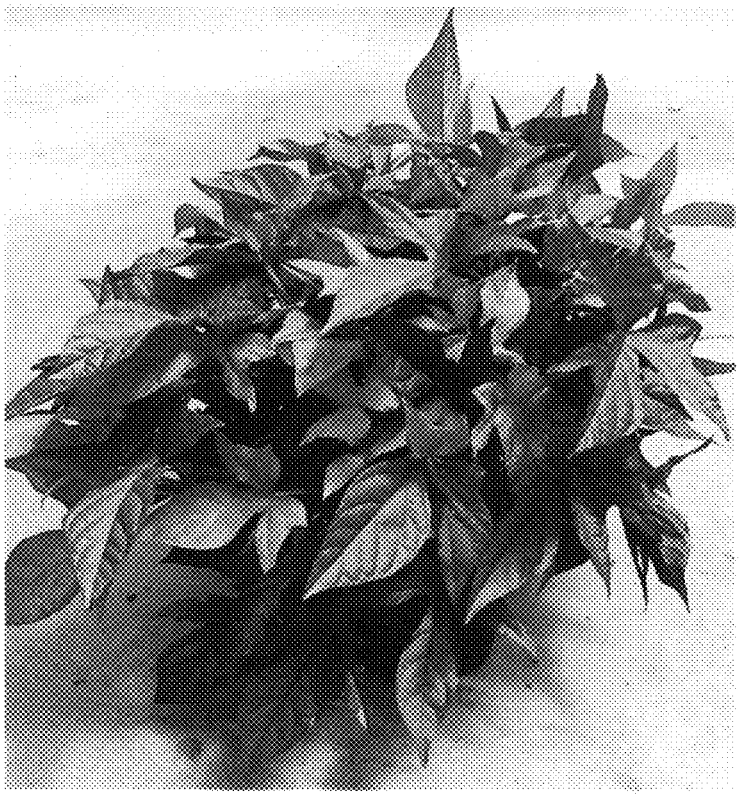

The photographic drawings show in FIG. 1, a close-up of the foliage, and in FIG. 2, a mature plant of the new variety.

DETAILED BOTANICAL DESCRIPTION

The aforementioned photographs were taken in April 2015 in Gilroy, Calif. The plants were growing in 11 cm pots on benches in a greenhouse. They were about 10 weeks of age.

Color chart used: Royal Horticultural Society Colour Chart (R.H.S.) 2001.

TABLE 1

DIFFERENCES BETWEEN THE NEW VARIETY 'KPOZ0001' AND A SIMILAR VARIETY

| | 'KPOZ0001' | 'Sweet Caroline Bronze' |
|---|---|---|
| Stem diameter: | Larger | Thinner |
| Internode length: | Shorter | Longer |
| Foliage size: | Larger | Smaller |
| Plant size: | More compact | More trailing |

Plant:

*Form, growth and habit.*—Compact and mounding plant habit that becomes more outwardly trailing with age, Freely branching with dense foliage.

*Height.*—22-25 cm.

*Width.*—25-32 cm.

Roots/tubers:

*Type.*—At the age of these plants used for the descriptive data, there were no real tubers forming. The roots themselves are thick, fleshy and cream to white.

Foliage:

*Type.*—Alternate, simple.

*Immature, leaf color, upper surface.*—RHS 146D, mottled and overlaid with RHS 165B. Lower surface: Closest to RHS 147C with some RHS 166B.

*Mature, leaf color, upper surface.*—RHS 148A heavily overlaid with anthocyanins closest to RHS 166A. Lower surface: Closest to RHS 146B heavily overlaid with RHS 72A.

*Color of veins, upper surface.*—RHS 187C.

*Color of veins, lower surface.*—RHS 187B.

*Length.*—13.0-15.0 cm.

*Width.*—12-16 cm.

*Shape.*—Roughly cordate; palmately, 5 lobed.

*Base shape.*—Auriculate.

*Apex shape.*—Apiculate.

*Margin.*—Entire.

*Texture.*—Hirsute on the margins of both surfaces.

*Petioles color.*—RHS 187C.

*Petioles length.*—9.5-14.5 cm.

*Diameter of petiole.*—0.4-0.5 cm.

*Texture.*—Glabrous.

Stem:

*Color of stem.*—RHS 187C.

*Length of stem.*—12-16 cm.

*Diameter.*—0.5-0.5 cm.

*Length of internodes.*—0.8-1.1 cm.

*Texture.*—Glabrous.

Inflorescence:

*Type.*—None present. Ephemeral; rarely see flowers. Flowers only under very strict short day lengths.

*Fragrance.*—None.

*Color of peduncle.*—RHS 187A but slightly lighter.

*Length of peduncle.*—2-4 cm.

*Peduncle diameter.*—0.2 cm.

*Texture.*—Glabrous.

Corolla:

*Form.*—Single trumpet-shaped flowers arise from leaf axils comprised of 5 petals fused at the corolla length and base.

*Flower diameter.*—3.5-3.7 cm.

*Flower depth.*—3.5-3.6 cm.

*Color of petals, upper surface.*—RHS 65D; RHS N155C margins; veins RHS N77B.

*Color of petals, lower surface.*—RHS 186C and D; RHS N155B margins.

*Length of petals.*—1.3-1.5 cm.

*Width of petals.*—1.2-1.3 cm.

*Petal shape.*—Obcordate.

*Apex shape.*—Acute.

*Margin.*—Entire.

*Petal texture.*—Papillose on upper surface and glabrous under.

*Corolla color inner surface.*—RHS N81D ground. color; RHS N80B basally; RHS N79B veining that fades to RHS N77B at petal lobes. Outer surface: RHS 186C and D, slightly striated and suffused together.

*Corolla diameter at flare.*—1.5-1.6 cm.

Bud (just before opening):

*Color.*—RHS 65C.

*Length.*—2.1-2.2 cm.

*Width.*—0.5-0.7 cm.

*Shape.*—Orbicular.

*Calyx.*—5 sepals fused at the base.

*Color of sepals, inner surface.*—Closest to RHS N186C Outer surface: Closest to RHS 145A, overlaid with anthocyanins of about RHS N186A-B.

*Length of sepals.*—0.7-0.8 cm.

*Width of sepals.*—0.2-03 cm.

*Sepal shape.*—Lanceolate.

*Apex shape.*—Acute.

*Margins.*—Entire.

*Texture.*—Slightly pubescent on the outer surface and glabrous on the inner surface.

Reproductive organs:

*Pistil.*—1.

*Length.*—1.3-1.5 cm.

*Style color.*—RHS N155B but whiter.

*Style length.*—1.2-1.3 cm.

*Stigma color.*—RHS N155B but whiter.

*Stamens.*—5.

*Color of filaments.*—RHS N155B but whiter.

*Length filaments.*—0.4 cm.

*Anther color.*—RHS 155C.

*Length of anthers.*—0.1-0.2 cm.

*Color of pollen.*—RHS 155A.

*Pollen amount.*—Scarce.

Fertility/seed set: Has not been observed to date.

Disease/pest resistance: Has not been observed to date.

What is claimed is:

1. A new and distinct variety of *Ipomoea* plant named 'KPOZ0001', substantially as illustrated and described herein.

* * * * *